United States Patent [19]

Maurer et al.

[11] 4,278,610

[45] Jul. 14, 1981

[54] METHOD OF MAKING AN ORGANIC METAL SALT OR COMPLEX

[75] Inventors: Gerald L. Maurer, Fairfield; Virginia E. Stefanini, Cincinnati, both of Ohio

[73] Assignee: National Research Laboratories, Cincinnati, Ohio

[21] Appl. No.: 105,623

[22] Filed: Dec. 20, 1979 (Under 37 CFR 1.47)

Related U.S. Application Data

[63] Continuation-in-part of Ser. No. 932,945, Aug. 11, 1978, abandoned.

[51] Int. Cl.³ .................................................. C07F 1/08
[52] U.S. Cl. ................................. 260/438.1; 260/414; 260/429 R; 260/429 J; 260/429 K; 260/429.9; 260/430; 260/431; 260/438.5 R; 260/439 R; 260/447; 260/448 R; 260/448 B
[58] Field of Search ............ 260/429 R, 429 J, 429.9, 260/438.1, 448 B, 414

[56] References Cited

U.S. PATENT DOCUMENTS

| | | | |
|---|---|---|---|
| 1,009,864 | 11/1911 | Schneider | 260/438.1 |
| 2,466,925 | 4/1949 | Brauner | 260/438.1 X |
| 2,999,878 | 9/1961 | Okawa et al. | 260/438.1 X |
| 3,062,719 | 11/1962 | Rubin et al. | 260/429 J |
| 3,142,702 | 7/1964 | Sawa et al. | 260/429 J |
| 3,200,136 | 8/1965 | Grossmith | 260/448 B X |
| 3,271,310 | 9/1966 | LeSuer | 260/438.1 X |
| 3,428,662 | 2/1969 | Millendorf et al. | 260/429 R |
| 3,476,786 | 11/1969 | Lally et al. | 260/414 X |
| 3,647,840 | 3/1972 | Biels | 260/438.1 |

*Primary Examiner*—Helen M. S. Sneed
*Attorney, Agent, or Firm*—Wood, Herron & Evans

[57] ABSTRACT

A method of making an organic metal salt or complex is disclosed by reacting a heavy metal hydroxide with an organic Lewis acid or salt thereof in the presence of a gaseous catalyst such as a form of $CO_2$. The reaction may be controlled by the addition of a buffering agent. Other gaseous catalysts such as CO and $SO_2$ or their related salts, can be employed. The method produces organic metal complexes or salts in a pure second salt-free state either in a solution or solid state.

25 Claims, No Drawings

METHOD OF MAKING AN ORGANIC METAL SALT OR COMPLEX

RELATED APPLICATION

This application is a continuation-in-part of application Ser. No. 932,945, filed Aug. 11, 1978, now abandoned by Gerald L. Maurer and Virginia E. Stefanini.

BACKGROUND OF THE INVENTION

Heavy metal salts or complexes of organic acids have commonly been prepared by reacting a heavy metal chloride or sulfate with an alkali metal salt of the acid. In these reactions, the usual by-product salts such as NaCl, $Na_2SO_4$, KCl, LiCl and $K_2SO_4$ are highly soluble in aqueous media. In the formation of metal complexes, it has been proposed to remove such by-product salts by a technique of extraction as, for example, disclosed in U.S. Pat. No. 4,055,655. However, such extraction techniques become difficult or even prohibitively expensive. The need for synthesizing second salt-free aqueous and solid preparations of heavy metal salts or chelates is high-lighted by a brief consideration of the end uses of such salts or chelates. For instance, in the case of employing such complexes as antimicrobial agents, the above-mentioned common second salts are all potentially irritating to normal skin, and markedly irritating to denuded or injured tissue. In industrial applications, such common salts are found to be corrosive to the metals in machinery and work pieces. Thus, a method for the production of metal salts or complexes of organic acids which are second salt-free would be highly desirable, particularly when such complexes are used in any application in which such salts may be potentially harmful or unwanted.

The classic heavy metal donors which are employed in prior art techniques are heavy metal chlorides or sulfates. These classic salts provide lower percentages by weight of the heavy metal ion in the salt in comparison, for example, to the corresponding heavy metal carbonates or hydroxides. For instance, the percent of copper in $CuCl_2 \cdot 2H_2O$ and $CuSO_4 \cdot 5H_2O$ is approximately 37 and 25%, respectively. In contrast, the percent of copper in copper hydroxide is approximately 80%. However, the copper hydroxide as a possible form of heavy metal donor, which potentially provides a more efficient source of heavy metal ion, is relatively inert.

SUMMARY OF THE INVENTION

This invention is directed to a method of making an organic metal salt or complex in a very efficient manner. According to the principles of this invention, heavy metal complexes or salts may be synthesized in a second salt-free aqueous or solid state. Furthermore, the invention enables the utilization of highly efficient heavy metal donors in the reaction with organic acids. Thus, this invention eliminates the need for utilization of classic heavy metal donors, such as the heavy metal chlorides, or sulfates, which provide highly soluble and undesirable by-products in industrial or pharmaceutical applications as developed above. These and other advantages will be further understood with reference to the following description.

In a broad aspect, the method of making an organic metal salt or complex according to this invention involves reacting a heavy metal hydroxide with an organic Lewis acid, or salt thereof, in the presence of a gaseous catalyst. A catalytic form of $CO_2$ has been found very desirable including carbonic acid, bicarbonate, carbonate and carbon dioxide, and mixtures thereof. Other gaseous catalysts such as CO and $SO_2$, or their salts can be used. There are several unique features of this method. For instance, in contrast to the rather classic prior art heavy metal chloride or sulfate donors which result in by-product salts, the method enables the preparation of second salt-free products. In addition, the method employs heavy metal hydroxides which heretofore have been considered relatively inert. The heavy metal hydroxides used according to the method also are more efficient due to their higher percentage of heavy metal ion compared to sulfates, chlorides and other common donors.

Another feature of this invention enables the use of efficient naturally-occurring metal donors. For instance, whereas a most efficient donor would be a heavy metal carbonate, heavy metal carbonates are frequently unavailable or prohibitively expensive. It has been found that basic metal carbonates having a general formula $xMCO_3 \cdot yM(OH)_2 \cdot zH_2O$, as commonly found in nature, offer an excellent source of starting material for the inventive reaction, thereby offering significant economies. Such basic metal carbonates offer two efficient sources of metal ion, the metal carbonate and hydroxide. For example, the copper carbonate salt in malachite has been found to provide an effective form of $CO_2$ which drives the heavy metal hydroxide to react with an organic Lewis acid, such as citric acid.

According to the techniques herein disclosed, heavy metal organic complexes or salts can be prepared in pure solution or solid forms. Such pure forms enable the wide utilization of metal complexes or salts, free from corrosion or other problems in industrial applications. Furthermore, purity may be obtained in solution form or reaction products may be isolated by direct crystallization to a pure solid state.

Another significant aspect of this invention is the provision of means or method for retaining a form of $CO_2$ in the reaction medium such that the reaction may be driven to completion. On one hand, the reaction may be conducted in a sealed reaction vessel or environment for retaining the $CO_2$ where it might otherwise escape. In another form, the reaction has been found capable of control with a buffering agent. By the employment of a buffering agent, the pH is controlled, thereby providing retained $CO_2$ to drive the reaction to completion.

The invention will be better understood with reference to chemical mechanisms believed to be involved. It is to be understood, however, that the empirical results stand on their own and applicants do not herein wish to be limited to specific mechanisms or theories. Still, unique features of this invention and the unexpected results achieved may be elucidated and a person of ordinary skill in this art may better understand the scope of the invention. Reference is first made to the utilization of basic carbonate salts of heavy metals, represented by the formula $xMCO_3 \cdot yM(OH)_2 \cdot zH_2O$, as metal donors for the preparation of chelates with polyfunctional organic ligands, e.g., citrate. In such a typical reaction, the metal carbonate is believed to react to form a bicarbonate ion, which undergoes an initial reaction onto the relatively unreaction $M(OH)_2$ group, apparently to form a more reactive $M(HCO_3)_2$ molecule which then dissolves to form a free metallic cation able to react with the organic ligand such as citrate. The following reaction sequence demonstrates the case of basic copper carbonate and a polyfunctional organic ligand, represented by the letter L.

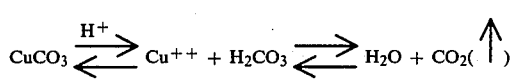

(1)

The rate of this reaction, and the resultant loss of $CO_2$, is controlled by a citrate buffer maintaining a mildly acidic pH in accordance with the most preferred method of this invention. Where the reaction is not contained, the carbonate lost as $CO_2$ must be replaced for utilization later in the reaction; therefore, a slower reaction rate for this step leads to a more efficient synthesis.

$$Cu^{++} + L^{=} \rightleftharpoons CuL^{-} \qquad (2)$$

This reaction, forming the 1:1 Cu:ligand chelate, is spontaneous under the pH conditions of the synthesis.

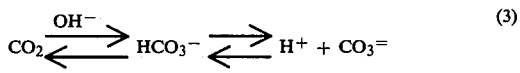

(3)

$$Cu(OH)_2 + 2HCO_3^- \rightleftharpoons Cu(HCO_3)_2 + 2OH^- \qquad (4)$$

The presumed existence of this addition product is supported by the formation, during the reaction, of a poorly soluble green-black material which gradually disappears. The eventual completion of this reaction depends upon the added bicarbonate ion, which replenishes the carbonate lost as $CO_2$ gas.

$$Cu(HCO_3)_2 \rightleftharpoons Cu^{++} + 2HCO_3^- \qquad (5)$$

The equilibrium for this reaction lies to the reactant side. Therefore, this reaction is probably the rate-limiting step of the synthesis. The reaction rate of this step is enhanced by the exhaustion of the product, $Cu^{++}$, as shown in Step 2 above, in the subsequent formation of the 1:1 complex.

$$HCO_3^- \rightleftharpoons CO_2(\uparrow) + OH^- \qquad (6)$$

This equilibrium reaction, which proceeds slowly to the right due to the slower rate of loss of the carbon dioxide in an only slightly acidic medium, is responsible for the eventual exhaustion of the carbonate counterion from the chelate preparation. The overall reaction is, then, $$Cu^{++} + L^{=} \rightleftharpoons CuL$$

In a preferred form of the method, the organic Lewis acid is prepared in an acidic solution. In the case of strongly acidic organic ligands, a buffer of pH 3.5–4.5 can be employed by mixing appropriate amounts of free organic acid and organic acid salt. In this pH range, the dissolution of a metal carbonate occurs quite slowly, and with little generation of carbon dioxide gas. Retention of carbon dioxide either as a soluble gas, or as a carbonate and/or bicarbonate enables the reaction to proceed slowly. Furthermore, it is desired to employ the most concentrated solutions practical with respect to solubility of reactants and reaction product. The more concentrated solution allows for enhanced reaction rate in Step 4 of the above reaction mechanism scheme, since a greater concentration of reactants allows for more frequent contact. The basic carbonate salt is added slowly to the organic acid solution to minimize foaming and resultant loss of the carbonate species. In an uncontained system some carbonate is lost, nonetheless, and it is usually replaced as bicarbonate ion, the form necessary for reaction in addition Step 4 above. $CO_2$ in the form of either sodium carbonate, dry ice, liquid $CO_2$, dissolved carbonate, or the like, is also adequate because of the usual equilibrium existing among the various forms. Because of the buffering capacity of a large number of organic acid ligands, adjustment of the pH during the reaction is rarely necessary. After the reaction is complete, the pH may be adjusted for storage or the solid form of the product may be isolated by direct crystallization.

Heavy metal hydroxides which are used in the method of this invention include those with a metal ion having a molecular number in excess of 4. Such metal ions may be of a monovalent or polyvalent nature, more specifically monovalent, bivalent, trivalent and other polyvalent cations including zinc, nickel, chromium, bismuth, mercury, silver, cobalt, magnesium, copper, aluminum and others. The term "heavy metal" as just defined thus also applies to the organic heavy metal salt or complex reaction product. The end use or industrial application will dictate the choice of heavy metal ion. In the case of antimicrobial agents, complexes of heavier metals are considered more toxic than those of lighter metals, for instance.

The term "organic Lewis acid" is used herein to denote any molecule or ion that can combine with another molecule or ion by forming a covalent chemical bond with two electrons from the second molecule or ion. Such a molecule or ion is thus an electron acceptor. Organic acids may either be of a monofunctional or polyfunctional type. For instance, typical examples include organic carboxylic acids, including monocarboxylic as well as dicarboxylic acids, or salts thereof characterized by the formula $(RCXX)_nM$ wherein the group RCXX is either a carboxylate or thiocarboxylate group of an aliphatic or aromatic mono or polyfunctional acid; R is a hydrocarbon or substituted hydrocarbon radical; X is oxygen or sulfur; n is an integral number usually from 1–3 and M is a mono or polyvalent metal. Aromatic carboxylates of the phthalic, benzoic or naphthoic type where R is aryl, diaryl or substituted aryl may be employed such as calcium benzoate or the like. Organic Lewis acids which can be employed for reaction with metal hydroxides include phosphorus acids, thiophosphorus acids, sulfur acids, sulfonic acids, and the like as well as corresponding alkali and alkaline earth metal salts thereof. Included in the acid class are phenates and a variety of other organic compounds such as amines, amides and alcohols. Illustrative of the carboxylic acids are palmitic acid, stearic acid, myristic acid, oleic acid, linoleic acid, behenic acid, hexatriacontanoic acid, tetrapropylene-substituted glutaric acid, succinic acid, octadecyl-substituted adipic acid, chlorostearic acid, 9-methylstearic acid, dichlorostearic acid, stearylbenzoic acid, naphthoic acid, dilauryldecahydronaphthalene carboxylic acid, didodecyltetralin carboxylic acid, dioctylcyclohexane carboxylic acid, mixtures of these acids, their alkali and alkaline earth metal salts and/or their anhydrides. Of the sulfonic acids, the mono-, di- and tri-aliphatic hydrocarbon substituted aryl sulfonic acids and the petroleum sulfonic acids (petro-sulfonic acids), mahogany sulfonic acids, petroleum sulfonic acids, monoeicosane-substituted naphthalene sulfonic acids, dodecylbenzene sulfonic acids, petrolatum sulfonic acids, dilauryl betanaphthalene sulfonic acids, paraffin wax sulfonic acid, cetylcyclopentane sulfonic acid, lauryl-cyclo-hexane sulfonic acids, polyethylene sulfonic acids, etc. Illustrative of the synthetically produced alkylated benzene and naphthalene sulfonic acids are those containing alkyl substituents having from 8 to about 30 carbon atoms therein. Such acids include di-isododecyl-benzene sulfonic acid, wax-substituted phenol sulfonic acid, wax-substituted benzene sulfonic acids, polybutene-substituted sulfonic acid, cetylchlorobenzene sulfonic acid, di-cetylnaphthalene sulfonic acid, di-lauryldiphenylether sulfonic acid, diisononylbenzene sulfonic acid, di-isooctadecylbenzene-sulfonic acid, stearylnaphthalene sulfonic acid, and the like. Such petroleum sulfonic acids, depending on the nature of the petroleum oils from which they are prepared, are oil-soluble alkane sulfonic acids, alkyl-substituted cycloaliphatic sulfonic acids, including cycloalkyl sulfonic acids, and cycloalkene sulfonic acids, and alkyl, alkaryl, or aralkyl substituted hydrocarbon aromatic sulfonic acids including single and condensed aromatic nuclei as well as partially hydrogenated forms thereof. Examples of such petrosulfonic acids include mahogany sulfonic acid, white oil sulfonic acid, petrolatum sulfonic acid, petroleum naphthene sulfonic acid, etc. An especially suitable group of aliphatic fatty acids includes the saturated and unsaturated higher fatty acids containing from 12 to about 30 carbon atoms. Illustrative of these acids are lauric acid, palmitic acid, oleic acid, linoleic acid, oleo-stearic acid, stearic acid, myristic acid, and undecalinic acid, alpha-chlorostearic acid, and alpha-nitrolauric acid. The organic acids may contain non-hydrocarbon substituents such as halo, nitro, alkoxy, hydroxyl, and the like.

A particularly useful class of metal complexes made according to the method of this invention are those where the metal hydroxide is reacted with a polyfunctional organic ligand. In the examples which follow, citric acid, mercaptosuccinic acid, ethylenediamine tetraacetic acid and others are used. However, other polyfunctional organic ligands may be substituted for such acids specifically exemplified by the operating examples which follow. Included among other polyfunctional ligands are the broader class of alpha or beta hydroxy polycarboxylic acids represented by citric acid. Also, other functionally substituted acids such as alpha or beta amino, sulfhydro, phosphenol, etc., can be substituted in the molecular model of the metal complexes of this invention. These metal complexes may be of the 1:1 type or wherein the ratio of the metal ion with respect to the polyfunctional ligand varies, as also represented by the dicupric edetate and dicobaltous edetate of the examples. Such metal complexes of polyfunctional organic ligands have been further disclosed in U.S. Pat. No. 4,055,655 at Columns 5 and 6, and such disclosures are incorporated herein by reference.

The following examples illustrate various embodiments of this invention.

EXAMPLE 1—Disodium Monocopper (II) Citrate Complex By Basic Copper Carbonate-Citric Acid-Sodium Bicarbonate Method INGREDIENTS:
 65 ml water
 61 g citric acid, anhydrous
 35 g basic copper carbonate [$CuCO_3 \cdot Cu(OH)_2 \cdot H_2O$]
 60 g sodium bicarbonate ($NaHCO_3$)

The citric acid was dissolved in the water. The basic copper carbonate was added with stirring and dispersed well. This mixture was allowed to react for approximately 10 minutes or until the foam ($CO_2$ generation) subsided. Sodium bicarbonate was added slowly with gentle mixing until the pH was between 5.5 and 6.0. The solution was mixed until a black granular precipitate was no longer visible [$Cu(HCO_3)_2$]. The remainder of the sodium bicarbonate was added slowly with gentle stirring to adjust the pH to 7.0 for storage. The soluble copper chelate was thus prepared free from a second salt.

EXAMPLE 2— Disodium Monocopper(II) Citrate Complex By Basic Copper Carbonate-Sodium Citrate-Dry Ice Method INGREDIENTS:
 75 ml 2.6 M aqueous trisodium citrate dihydrate adjusted to pH 5.0 with 2.6 M aqueous citric acid
 47.8 g basic copper carbonate [$CuCO_3 \cdot Cu(OH)_2 \cdot H_2O$]
 ca. 80 g dry ice ($CO_2$) pellets
 NaOH flakes The basic copper carbonate was added slowly to the citrate solution with rapid mixing to effect good dispersion. This mixture was allowed to react for approximately 10 minutes, or until the foam ($CO_2$ generation subsided. The dry ice was added slowly with constant stirring, over a 10 minute period. The solution was mixed vigorously for approximately 1 hour or until a granular black precipitate [$Cu(HCO_3)_2$] was no longer visible. For storage of the soluble copper chelate, the pH was adjusted to between 6.5 and 7.0 with NaOH.

EXAMPLE 3— Disodium Monocopper(II) Citrate Complex By Basic Copper Carbonate-Citric Acid-Dry Ice Method INGREDIENTS:
 50 ml water
 61 g citric acid, anhydrous
 35 g basic copper carbonate [$CuCO_3 \cdot Cu(OH)_2 \cdot H_2O$]
 60 g dry ice pellets ($CO_2$)
 47 g NaOH flakes The citric acid was dissolved in the water. The basic copper carbonate was added to effect homogeneous dispersion. The mixture was allowed to react for approximately 10 minutes, or until the foam ($CO_2$ generation) subsides. The dry ice was added slowly with constant stirring. The material was allowed to mix until a black granular precipitate was no longer seen [$Cu(HCO_3)_2$]. NaOH flakes were added slowly so that heat generation did not become excessive. The pH of the resultant solution was approximately 7.0, ideal for storage.

EXAMPLE 4— Copper 3,3'-Thiodipropionate By Basic Copper Carbonate-3,3'-Thiodipropionic Acid-Sodium Bicarbonate Method INGREDIENTS:
 100 ml water
 1.2 g basic copper carbonate
 1.78 g 3,3'-thiodipropionic acid, anhydrous
 ca 0.1 g sodium bicarbonate, anhydrous The 3,3'-thiodipropionic acid was dissolved in the water. The basic copper carbonate was added slowly with stirring. Gradual evolution of bubbles occurred after enough of the metal salt had been added to raise the pH to ca. 3.2. At this point, the insoluble material began to disappear more rapidly. After all of the bubbling had stopped, the liquid was stirred for approximately 15 minutes, and then the sodium bicarbonate was added slowly, with ample reaction time before any further addition. The reaction was complete when a clear blue-green solution was obtained.

EXAMPLE 5— Cobaltous Mercaptosuccinate By Basic Cobaltous Carbonate-Mercaptosuccinic Acid-Sodium Bicarbonate Method INGREDIENTS:
 30 ml hot water
 1.03 g basic cobaltous carbonate
 1.50 g mercaptosuccinic acid
 0.2 g sodium bicarbonate
 concentrated aqueous NaOH solution The acid was dissolved in the water, and the cobaltous carbonate was added slowly with vigorous stirring. Gradual development of a rust-brown color was noticeable followed by a deep brown coloration of the supernatant liquid. After all of the cobaltous carbonate was added, the mixture was allowed to react for 30–40 minutes, and then the sodium bicarbonate was added very slowly to minimize foaming. When all of the insoluble material was gone, the pH was adjusted with concentrated NaOH solution.

EXAMPLE 6— Dicopper Edetate By Basic Copper Carbonate-Disodium Edetate Method INGREDIENTS:
 100 ml water
 2.39 g basic copper carbonate
 3.72 g disodium edetate dihydrate The disodium edetate was dissolved in the water. The basic copper carbonate was added slowly. The reaction was complete when no undissolved green material remained. In contrast to Examples 1–5, the chelate formed by the method of this example involved two copper ions per ligand molecule.

EXAMPLE 7— Dicobaltous Edetate By Basic Cobaltous Carbonate-Disodium Edetate-Sodium Bicarbonate Method INGREDIENTS:
 50 ml water
 2.07 g basic cobaltous carbonate, anhydrous
 3.72 g disodium edetate, dihydrate
 trace, sodium bicarbonate, anhydrous The disodium edetate was dissolved in the water. The cobaltous carbonate was added slowly with stirring. Gradual evolution of bubbles occurred after enough of the metal salt had been added to raise the pH to roughly 5. At that point, the insoluble material began to disappear more rapidly. After all of the bubbling had stopped, the liquid was stirred for approximately 15 minutes, and then the sodium bicarbonate was added slowly, with ample reaction time before further addition. The reaction was complete when a clear pink solution was obtained.

EXAMPLE 8— Copper Dithizone By Basic Copper Carbonate-Dithizone Method

INGREDIENTS:
 5 ml water
 20 ml chloroform
 12.0 mg basic copper carbonate
 25.6 mg dithizone The dithizone was dissolved in the chloroform and the water was added. The basic copper carbonate was added and dispersed in the aqueous phase. The mixture was stirred well until no basic copper carbonate was visible in the aqueous phase when the phases were allowed to separate. This example also illustrates that the formation of the copper dithizone chelate can take place in non-aqueous media.

EXAMPLE 9— Cupric Caprylate By Basic Copper Carbonate-Caprylic Acid-$CO_2$ Gas Method INGREDIENTS:
 23.9 g basic copper carbonate (1.10 mole)
 57.7 g caprylic acid (0.4 mole)
 50 ml methanol
 carbon dioxide gas The basic copper carbonate was suspended in the methanol with vigorous stirring. The caprylic acid was added. The mixture was allowed to react with stirring. After the reaction appeared complete, the $CO_2$ was bubbled in very slowly until no further change took place. A greenish powder was isolated by washing the mixture with distilled water and vacuum drying.

Evolution of gas occurred during the initial stage of the reaction, with the formation of bubbles on the surface of the suspended salt. A definite color change took place. The pH immediately after the addition of the carboxylic acid was 4.6. Before the bubbling of the $CO_2$ into the mixture was begun, the pH was 5.7. While $CO_2$ was being bubbled into the mixture, the pH was 4.6. The reaction continued roughly 12 hours.

The isolated product was soluble (ca 1 g/100 ml) in octanol. By comparison, basic copper carbonate is not soluble in octanol.

EXAMPLE 10— Aluminum Salicylate By Sodium Bicarbonate-Salicyclic Acid Method INGREDIENTS:
 0.038 g $Al(OH)_3$ (dried into a soluble, friable powder by gentle heating)
 0.20 g salicyclic acid
 0.002 g $NaHCO_3$
 100 ml distilled water
 NaOH solution A. Salicylic acid was dissolved in the water. The aluminum hydroxide was added and suspended well. The $NaHCO_3$ was added, and the vessel was sealed immediately and agitated for 8 hours. The solution was adjusted to pH 8.0 for storage.

B. The above ingredients used in paragraph A were combined for another procedure in which the vessel was left open and the mixture stirred vigorously, immediately after addition of the $NaHCO_3$, to permit $CO_2$ gas to escape. The vessel was agitated for 8 hours and its contents adjusted to pH 8.0. This material was compared to the product of paragraph A. The material in the open vessel was a very cloudy white gelatinous suspension typical of aluminum hydroxide colloids. The material in the closed vessel was a low viscosity liquid, with a very slight haze. The hazy material was thought to be aluminum complex that had not finished reacting to form aluminum salicylate.

EXAMPLE 11— Silver Salicylate by Sodium Bicarbonate-Salicylic Acid Method

INGREDIENTS:
0.1 g AgOH, Hydrous
0.1 g Salicylic acid
50 ml $H_2O$
0.06 g $NaHCO_3$,
NaOH solution Salicylic acid was dissolved in water. The AgOH was ground into a fine powder and then added slowly to the solution with vigorous stirring. After all of the material was well suspended, the $NaHCO_3$ was added and the vessel was sealed immediately and placed in a dark area. The material in the vessel was agitated for 8 hours to produce silver salicylate.

Evaluation of the Reactivity of Copper Hydroxide with Citric Acid in the Presence and Absence of Bicarbonate Ion For the purpose of further illustrating the reaction occurring between $Cu(OH)_2$ and citric acid when basic copper carbonate is added to the acid, it was decided to isolate the $Cu(OH)_2$ moiety of basic copper carbonate and react this with citric acid in the presence and absence of sodium bicarbonate.

To prepare $Cu(OH)_2$ essentially free of $CuCO_3$, 0.1 mole of the mixed salt was reacted with excess HCl to bring the pH to 2.0. Gas evolved for about 10 minutes. The green supernatant solution was decanted and the green solid precipitate was collected, washed four times with distilled water (at ten times original volume) and collected for centrifugation. The solid was assumed to be $Cu(OH)_2 \cdot xH_2O$.

The reaction mixtures were prepared as follows, in separate culture tubes:

| Tube 1 | Tube 2 |
|---|---|
| 20 mM $Cu(OH)_2 \cdot xH_2O$ | 20 mM $Cu(OH)_2 \cdot xH_2O$ |
| 20 mM citric acid blank | 20 mM citric acid |
| 8 ml water | 1.2 mM $NaHCO_3$ |
| | 8 ml water |

The pH of the contents of Tube 2 was 2.6, and that of Tube 1 only 2.0. Therefore, NaOH solution was added to raise the pH of the contents of Tube 1 to 2.6. Both tubes were placed on a mechanical agitator for 8 hours with Tube 1 open and Tube 2 sealed to retain the sodium bicarbonate in the aqueous phase. At the end of this period, Tube 1 was sealed and Tube 2 allowed to stand overnight.

The following day, the pH of each mixture was adjusted to 8.0 with 4 normal NaOH solution, i.e., 3 ml were added to Tube 1 and 12 ml were added to Tube 2. The tubes were centrifuged to sediment any insoluble material. In Tube 1, a very pale blue supernatant liquid was found, with approximately 1.0 ml of pale green sediment, the color of the starting $CuOH_2$. In Tube 2, a dark blue supernatant (the color of the product formed from the reaction of citric acid and basic copper carbonate) was found, with about 0.2 ml of a green-black sediment.

Several conclusions were drawn from the above results. It was verified that the sediment in Tube 1 was unreacted $Cu(OH)_2 \cdot xH_2O$. The small amount of conversion of $Cu(OH)_2$ taking place in Tube 1 was due to contaminating $CuCO_3$ in the $Cu(OH)_2$ preparation. In Tube 2, 1:1 Cu-citrate complex was formed and verified. The green-black sediment found in Tube 2 was the product of the "activation" of $Cu(OH)_2$ caused by the action of the $NaHCO_3$, and possibly the citric acid as well. If additional reaction time had been given the contents of Tube 2, the green-black material would have been converted into the 1:1 complex as has been verified by further experimental work.

Evaluation of Other Gaseous Catalysts and Organic Acids

In the above examples, carbon dioxide gas, and related salts such as $Na_2CO_3$ and $NaHCO_3$ have been proved to act catalytically in the conversion of metal hydroxides to organo-metallic compounds. To demonstrate the catalytic activity of other gases in the reaction system, two other gases, CO and $SO_2$ have been examined as follows. Included as controls for these examples are $CO_2$, a catalytic gas as above demonstrated, and $N_2$, which has been found to be non-catalytic in this reaction.

In the following series of experiments, further proof for the catalytic nature of the gases' activity in the reaction system is offered. Far less than stoichiometric amounts of the gaseous molecules exert a great effect on formation of the complexes with respect to reduction in reaction time as well as the exploitation of otherwise poorly reactive cation donors such as hydroxides of polyvalent metal ions. Another great benefit derived from the unexpected activity of these gaseous catalysts lies primarily in the formation of second salt-free products.

Screw-capped borosilicate glass tubes, 16×125 mm, were used as reaction vessels. To each of 12 tubes was added 1.0 ml of a 1000 mM suspension of $Cu(OH)_2$, prepared as above, representing 635 mg or 10 mMoles of $Cu^{++}$. A 1000 mM aqueous solution was prepared of each of the three acids used, citric acid, gluconic acid, and 1-naphthol-3, 6-disulfonic acid; and 2.0 ml of each solution were pipetted into four tubes. Immediately thereafter, 3.0 ml of freshly boiled distilled water were added to each tube. Following the filling of the tubes with reagents, nitrogen gas ($N_2$) was streamed gently into the liquid to flush out room air. A tight-fitting silicone rubber septum was fitted to the opening of each tube to preserve the atmosphere. Gaseous catalysts were introduced through a specially-designed three-way stopcock/hypodermic needle/syringe apparatus. The following technique was used to introduce a measured amount of gas into tubes:

(a) 15 cc of gas were allowed to flow into the syringe and equilibrate at atmospheric pressure, and the stopcock was closed;
(b) the syringe needle was thrust through the septum;
(c) the stopcock was adjusted to allow flow from the syringe through the needle into the dead space above the liquid;
(d) the gas was injected slowly; and
(e) the stopcock was closed and the needle withdrawn.

Subsequent tests indicated that the internal pressure of the tubes was approximately 28 psig (1.9 ATM).

The tubes were agitated on a rotator for an eight-hour period at roughly 180 rpm. Following this reaction time, the tubes were centrifuged to allow any insoluble material to settle. Gas pressure was checked using a gauge assembly attached to a syringe needle. It was found that the internal pressure was the same as initially, within a 3% limit of error.

The septa were removed from the reaction tubes and aliquots were withdrawn from the clear supernatant fluid for analysis of copper. An increase in soluble copper content in the $SO_2-$, $CO-$ and $CO_2$-containing tubes relative to the $N_2$-containing tubes would indicate catalytic activities of these gases. Soluble copper content was determined by the ammonia-diethyldithiocarbamate method, which yields a colored complex at 650 nm.

The results of the copper analyses are shown in the table below.

TABLE

Reactivity of $Cu(OH)_2$ in the Presence of Different Gases and Acids

|  | mg $Cu^{++}$ Reacted | mMoles $Cu^{++}$ Reacted | % Cu Reacted | Difference Over $N_2$ tube |
|---|---|---|---|---|
| Sulfonic Acid |  |  |  |  |
| $N_2$ | 76 | 1.2 | 12 | — |
| $CO_2$ | 247 | 3.9 | 39 | 3.25 x |
| CO | 95 | 1.5 | 15 | 1.25 x |
| $SO_2$ | 368 | 5.8 | 58 | 4.83 x |
| Gluconic Acid |  |  |  |  |
| $N_2$ | 247 | 3.9 | 39 | — |
| $CO_2$ | 368 | 5.8 | 58 | 1.49 x |
| CO | 337 | 5.3 | 53 | 1.36 x |
| $SO_2$ | 368 | 5.8 | 58 | 1.49 x |
| Citric Acid |  |  |  |  |
| $N_2$ | 133 | 2.1 | 21 | — |
| $CO_2$ | 521 | 8.2 | 82 | 3.90 x |
| CO | 368 | 5.8 | 58 | 2.76 x |
| $SO_2$ | 603 | 9.5 | 95 | 4.52 x |

Referring to the Table, the results clearly demonstrate the ability of CO, $CO_2$ and $SO_2$ to catalyze the conversion of metal hydroxides into organo-metallic compounds. The varying degrees of conversion of the hydroxides seen in the $N_2$-containing tubes are due to both a small amount of contamination of the hydroxide and the copper carbonate with which it is found in nature, and the slow non-catalytic conversion of the hydroxide which may occur in the presence of certain acid counter-ions.

It is also important to note from the Table the non-stoichiometric relationship of the catalytic gas to the amount of copper reacted. Only 0.675 mMole of gas was present in each reaction tube; however, the amount of copper converted ranged from 1.5 mMoles to 9.5 mMoles. Therefore, the ratio of the ion converted to the gas provided varied from 2.2 to as much as 14. Clearly, no stoichiometric relationship exists, and the function of the gases is catalytic.

In view of the above description and operating examples, this invention and its parameters will be understood. The method of reacting a heavy metal hydroxide and an organic Lewis acid in the presence of a gaseous catalyst has been described. The unique behavior of the gaseous catalyst enables the otherwise relatively inert metal hydroxide to react. The results suggest catalytic action because the gas participates in the reaction, but it is not consumed and may be recovered. A very unique aspect of this invention, thus, is the inclusion of a gas that accelerates the reaction and yet is removable or even evolves during reaction. This activity is also considered unique and unexpected. Other forms of the invention, as well as specific reaction materials will be understood to a person of ordinary skill in the art in view of the above description and operating examples.

What is claimed is:

1. Method of making an organic metal salt or complex comprising reacting a heavy metal hydroxide with an organic Lewis acid, or salt thereof, in an aqueous reaction medium and in the presence of a gaseous catalyst.

2. The method of claim 1 wherein said catalyst is a form of $CO_2$.

3. The method of claim 2 wherein said reaction is conducted in a buffered acidic medium.

4. The method of claim 1 wherein said catalyst is volatilized from the reaction.

5. The method of claim 1 selected from the group of $CO_2$, CO and $SO_2$.

6. Method of making an organic metal salt or complex comprising reacting a heavy metal hydroxide with an organic Lewis acid, or salt thereof, in an aqueous reaction medium and in the presence of a gaseous catalyst comprising a form of $CO_2$ selected from the group consisting of carbonic acid, bicarbonate, carbonate and carbon dioxide, and mixtures thereof.

7. The method of claim 6 wherein said heavy metal hydroxide is mixed with a heavy metal salt of carbonic acid which provides said form of $CO_2$.

8. The method of claim 7 comprising the further step of adding a form of $CO_2$ to the reaction.

9. The method of claim 6 which includes retaining $CO_2$ during the reaction.

10. The method of claim 6 with the further addition of a buffering agent to control the reaction.

11. The method of claim 6 conducted to obtain the organic metal complex or salt in a pure second salt-free state.

12. The method of claim 6 wherein said pure form is isolated by direct crystallization to a pure solid.

13. The method of claim 6 wherein said heavy metal is selected from the group consisting of zinc, nickel, chromium, bismuth, mercury, silver, copper, magnesium, aluminium and cobalt.

14. The method of claim 6 wherein said organic Lewis acid is selected from the group consisting of an organic acid and a substituted organic acid.

15. The method of claim 14 wherein said substituted organic acid is selected from the group consisting of hydroxypolycarboxylic, aminopolycarboxylic, sulfhydropolycarboxylic and phosphenolpolycarboxylic.

16. The method of claim 6 wherein the product of the reaction is a dialkali metal monoheavy metal chelate of an alpha-hydroxypolycarboxylic acid.

17. The method of claim 16 wherein said chelate is a dialkali metal monocopper(II) citrate.

18. The method of claim 17 wherein said chelate is in aqueous admixture.

19. The method of claim 17 wherein said chelate is a solid.

20. A method of making an organic metal complex or salt in a second salt-free state comprising
providing an aqueous reaction medium containing an organic Lewis acid solution containing a heavy metal hydroxide,
adding a gaseous catalyst selected from the group of $CO_2$, $SO_2$ and CO, and retaining said gaseous catalyst until said reaction is substantially complete to provide said second salt-free product.

21. The method of claim 20 wherein a heavy metal salt of carbonic acid provides said gaseous catalyst comprising a form of $CO_2$.

22. The method of claim 21 wherein the heavy metal hydroxide and carbonic acid salt are provided in the reaction medium as mixed salts.

23. The method of claim 20 wherein a buffering agent is added to control the reaction.

24. The method of claim 20 wherein said Lewis acid is selected from the group consisting of hydroxypolycarboxylic, aminopolycarboxylic, sulfhydropolycarboxylic, and phosphenolpolycarboxylic.

25. The method of claim 20 wherein said Lewis acid is selected from the group consisting of citric acid, gluconic acid, and 1-naphthol-3, 6-disulfonic acid.

* * * * *